United States Patent
Shukla et al.

(10) Patent No.: US 6,708,054 B2
(45) Date of Patent: Mar. 16, 2004

(54) MR-BASED REAL-TIME RADIATION THERAPY ONCOLOGY SIMULATOR

(75) Inventors: Himanshu P. Shukla, Gates Mills, OH (US); Michael C. Steckner, Richmond Heights, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 205 days.

(21) Appl. No.: 09/833,979

(22) Filed: Apr. 12, 2001

(65) Prior Publication Data

US 2002/0151786 A1 Oct. 17, 2002

(51) Int. Cl.⁷ .................................. A61B 5/05
(52) U.S. Cl. ..................... 600/411; 600/427; 378/65
(58) Field of Search .......................... 600/411, 427, 600/410, 414, 417, 436, 407, 421; 606/130; 128/869, 870, 585; 378/205–206, 64–65; 428/920

(56) References Cited

U.S. PATENT DOCUMENTS 5,553,112 A * 9/1996 Hardy et al. ................ 378/206
5,800,353 A    9/1998 McLaurin, Jr. ............. 600/407
5,807,254 A    9/1998 Meulenbrugge et al. .... 600/411
5,947,981 A    9/1999 Cosman ..................... 606/130
6,405,072 B1 * 6/2002 Cosman ..................... 600/426

FOREIGN PATENT DOCUMENTS

JP        08318001        12/1996
JP      2001291091        10/2001

* cited by examiner

Primary Examiner—Sang Paik
Assistant Examiner—Quang Van
(74) Attorney, Agent, or Firm—Fay, Sharpe, Fagan, Minnich & McKee, LLP

(57) ABSTRACT

In radiation oncology, a magnetic resonance apparatus is used to plan a treatment regimen. The oncologist uses the features of slice width selection, and depth selection to better ascertain where a medical malignancy is within a patient. In order to facilitate a user-friendly atmosphere for the oncologist, a new user control interface (50) is added to an MRI apparatus that includes controls normally found on a typical oncology linear accelerator. A conversion algorithm (52) translates the linac input into an imaging region for a magnetic resonance sequence that images the malignancy. Along each planned treatment trajectory radiation and MR projection images are superimposed to delineate the malignancy clearly for beam aiming and collimation adjustments.

25 Claims, 1 Drawing Sheet

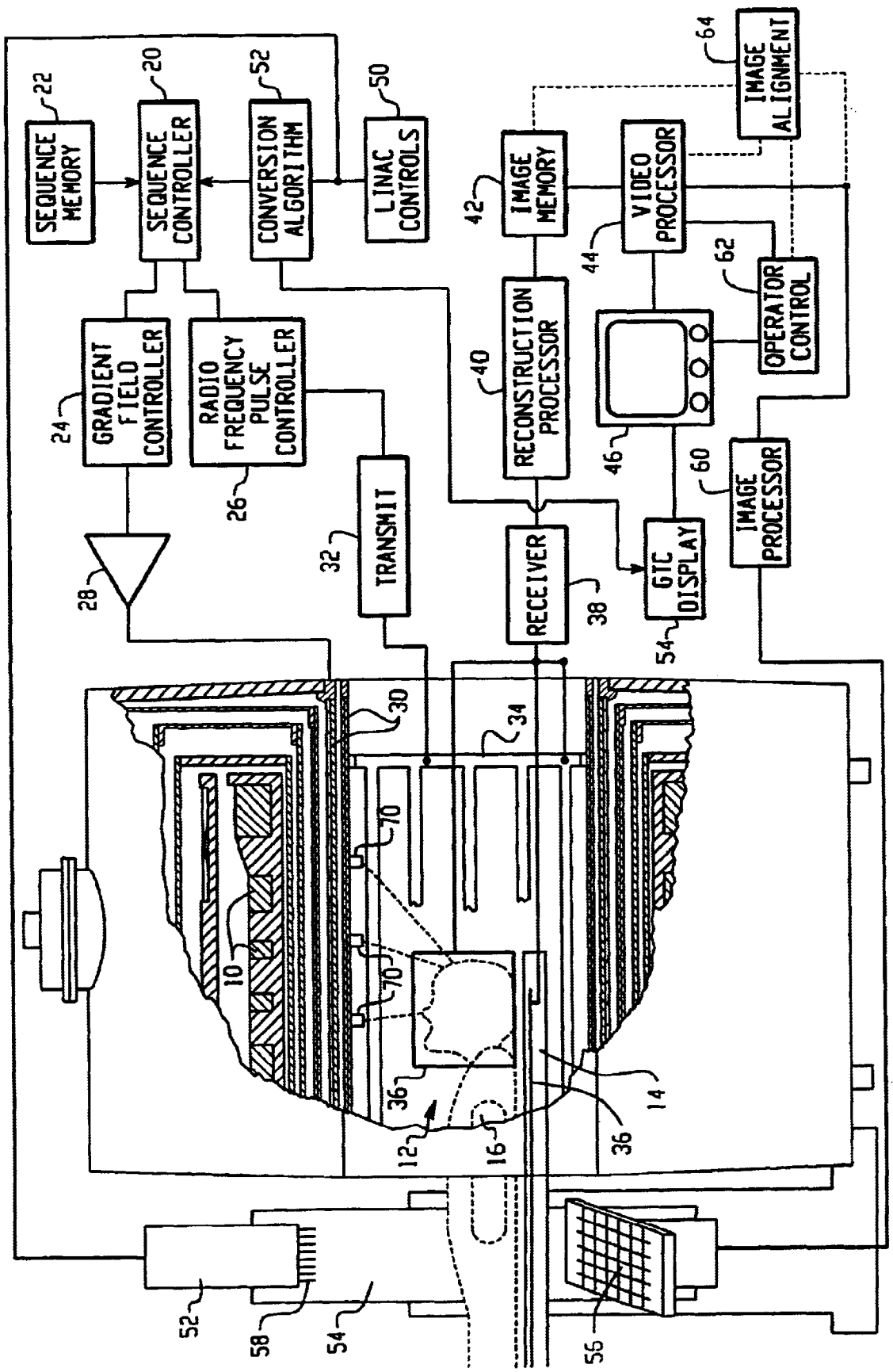

MR-BASED REAL-TIME RADIATION THERAPY ONCOLOGY SIMULATOR

BACKGROUND OF THE INVENTION

The present invention relates to the diagnostic imaging arts. It finds particular application in conjunction with diagnostic imaging in MRI scanners for oncology treatment applications and will be described with particular reference thereto. It will be appreciated, however, that the invention is also applicable to other types of diagnostic oncological imaging and for other diagnostic imaging for other purposes.

In oncological planning, the oncologist typically generates a plurality of x-ray, projection images of a region to be treated. The images show bone and other internal structures, but do not necessarily differentiate the tumor from non-cancerous tissue. However, from an apriori knowledge of anatomy and the nature of the carcinoma, the oncologist estimates the center of the tumor and its size (diameter).

One of the priorities in oncological procedures is accurately aligning a high power tumor killing x-ray beam with the internal tumor. If the selected trajectory is even slightly off, the x-ray beam will treat most of the tumor, but leave a small segment un-irradiated and damage healthy tissue. Un-irradiated tumor tissue can survive the treatment.

The oncologist determines a plurality of trajectories through the tumor which miss neighboring radiation sensitive tissue or radiation attenuating bone. Once the trajectories and points of entry into the patient have been determined, the oncologist positions a linear accelerator (linac) to aim its high energy x-ray beam to enter the patient at the selected point of entry and follow a selected trajectory. Optionally, after the linac is aimed, the operator opens the collimator and reduces the energy of the beam. An x-ray detector is positioned to receive the beam and generate a projection image of the irradiated region. If this shadowgram shows proper alignment, the beam is narrowed and its energy increased for treatment. Ideally, the x-ray beam is collimated to have a diameter slightly larger than the tumor to be irradiated. Making the diameter of the beam too large is detrimental in that it irradiates and harms healthy tissue. Making the beam diameter smaller increases a probability that cancerous tissue goes unirradiated. The more precisely the size, shape, and position of the tumor are known, the narrower the treatment beam can be collimated to minimize the irradiation of surrounding tissue while assuring the irradiation of all cancerous tissue. Because the oncologist is estimating the size and location of the tumor without precise visual confirmation, the treatment beam is typically wider than necessary to assure all cancerous tissue is irradiated.

Typically, the treatment process is repeated through a plurality of different trajectories to maximize the radiation at the tumor while minimizing radiation through surrounding tissue.

The present invention provides a new and improved method and apparatus which overcomes the above-referenced problems and others.

SUMMARY OF THE INVENTION

In accordance with one aspect of the present invention, a diagnostic imaging system is given. A magnetic resonance scanner generates an image of a portion of a patient including a medical malignancy. An operator inputs requests using a user interface having controls of a typical oncology linac. A coordinate conversion algorithm converts the input from the user interface into a form that can be utilized by the magnetic resonance scanner. A video processor withdraws selected portions of the image and converts them into a form suitable for a human readable display.

In accordance with another aspect of the present invention, a method of diagnostic imaging is given. Oncology linac controls are used to indicate a candidate treatment route through a patient. Control signals from the linac controls are converted in control signals for a magnetic resonance apparatus. A projection image along the treatment route is generated and displayed.

In accordance with another aspect of the present invention, an oncological treatment system is given. A high voltage linac is used to irradiate a malignancy in a patient, and a magnetic resonance apparatus is used for planning a procedure.

In accordance with another aspect of the present invention, an MRI hardware upgrade is given. A control panel with controls similar to those of a linear accelerator used for oncology purposes is translated by a conversion algorithm from a gantry, table, collimator coordinate system to a conventional MR slice center, orientation coordinate system.

One advantage of the present invention resides in its improved differentiation of soft tissue.

Another advantage of the present invention is that it facilitates a reduction in radiation doses in oncological treatments.

Another advantage of the present invention is that it facilitates location of internal patient structures from the exterior of the patient based on diagnostic images.

Another advantage of the present invention is that it reduces total patient radiation dose relative to x-ray and CT diagnostic imaging techniques.

Another advantage resides in the ability to control slice thickness and depth.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIG. 1 is a diagrammatic illustration of a magnetic resonance portion of an oncology treatment system in accordance with the present invention.

DETAILED DESCRIPTION OF THE PREFERRED EMBODIMENT

With reference to FIG. 1, a magnetic resonance diagnostic imaging apparatus generates a volumetric image of an internal region of the patient including a medical malignancy such as a cancerous tumor. A high field, bore type imaging system is illustrated although open magnet systems are also contemplated. If conditions permit, a real time or quasi-real time image is preferred. The diagnostic imager is used to locate the malignancy and record its position relative to the surrounding anatomy so that it may later be irradiated by an oncological treatment linac.

The diagnostic imager in the illustrated embodiment is a horizontal field magnetic resonance imaging system that includes a solenoidal, preferably superconducting, magnet 10. As a practical matter, horizontal field machines are preferable because they utilize a higher field than present day vertical field machines. The higher fields facilitate faster, higher resolution imaging. It is preferable that the patient remain in the same position throughout the planning session to facilitate alignment with the linac coordinate system. The magnet 10 generates a horizontal magnetic field through an imaging region 12 along the axis of its bore. A patient support 14 is movable in and out of the bore to position a region of interest of a subject 16 in the imaging region 12. Alternately, open field magnets present an open imaging volume which permit the positioning of the patient in an orientation he will be in for treatment.

A sequence control processor 20 retrieves a desired sequence from a sequence memory 22. The sequence control processor 20 transmits the desired sequence to a gradient field controller 24 and a radio frequency pulse controller 26. The controllers 24, 26 construct pulses in accordance with the desired sequence. The pulses from the gradient field controller are amplified by gradient field amplifiers 28 and excite a gradient coil 30, which imposes the desired gradient field on the main magnetic field. The pulses from the radio frequency pulse controller are transmitted by an RF transmitter 32 which excites an RF coil 34.

Magnetic resonance signals induced and manipulated by the RF pulses are received by the RF coil 34 or by other local receive coils 36. The signals are demodulated by at least one receiver 38 and reconstructed by a reconstruction processor 40 into an electronic image representation. The image representation is stored in a volumetric image memory 42 until such time when desired portions are selected and processed by a video processor 44 into a form suitable for a human readable display 46 such as a video monitor. In the preferred embodiment, images are displayed as they are reconstructed to form the closest to real time images as possible.

First, a volume image is generated for treatment planning. Once the trajectories have been selected, MR projection images are generated along each trajectory as described more fully below.

In order to facilitate oncologist user-friendliness, a linac controller controls position and operates like a linear accelerator 52, a supporting C-arm 54, and a two dimensional x-ray detector 56. The interface has the typical analog dials or numeric controls of an oncological linac. However, unlike a traditional linac control panel, the user interface 50 also includes slice thickness or slab selection controls, and depth selection controls for the MRI system. The operator may also choose the type of sequence, such as bone-emphasizing, tumor differentiation, and the like. For example, given a tumor that is constructed of the same type of tissue that surrounds it, the only difference may be the density of the tissue, because the cancerous cells divide more rapidly then the normal ones. In this case, the operator can select a sequence that clearly contrasts the tissue densities.

The MRI machine has the ability to image in any arbitrary direction, view from any angle, and control slice depth and position. The linac simulators used for oncology are not as versatile. Typically, an oncology linac x-ray simulator has three inputs: gantry, table, and collimator. The gantry input specifies an angular orientation of the simulator and C-arm around the patient and a canting of the plane of the C-arm relative to a longitudinal axis of the patient. The table of an oncology linac simulator can typically move in three directions, up-down, longitudinally back and forth, and canting relative to a longitudinal axis of the patient. Finally, the collimator input adjusts the angle of a collimator 58 and a size of an aperture opening. This makes the beam of x-rays wide or narrow, depending on the desired path and diameter.

The user interface 50 translates these control settings into corresponding MRI machine settings. The MRI machine is not using penetrating radiation to image, and does not use the same coordinate system. A conversion algorithm 52 takes the input in terms of gantry, table, and collimator and translates it into terms of a slice center and an orientation. The sequence controller 20 modifies a selected magnetic resonance sequence from the sequence memory 22 that images the area to shift and rotate the imaged volume and coordinates as input by the operator. For real time imaging, projection images are generated. That is, the data is not phase encoded in one dimension resulting in projection images. More specifically, the operator selects an imaging sequence that emphasizes the tumor. Preferably, a sequence that emphasizes both the tumor and bone is selected. The result is a magnetic resonance projection image of the same region that an x-ray apparatus would have yielded, given the same inputs, but including tissue that is difficult to image or differentiate with x-rays. That is, a beam's eye view of the region is generated. When the image is displayed, a G.T.C. (Gantry, Table, Collimator) display 54 gives the position of the current projection image in terms of gantry, table, and collimator.

Once the beam trajectory is decided, the projection MRI image is saved. The patient and linac are positioned to irradiate along the same trajectory. As the linac is operated at a low power, the detector 56 generates x-ray projection data. An x-ray image processor 60 processes the x-ray data and the video processor 44 converts the x-ray image representation into appropriate format for the monitor 46. The corresponding MRI and x-ray projection images are displayed side by side in one embodiment. An operator control 62 enables the operator to manipulate the two images including superimposing them.

Superimposition effectively places the clear MRI differentiated tumor into the x-ray image. Preferably x-ray beam characteristics, such as center and diameter are also superimposed on the image. Optionally, an alignment processor 64 compares corresponding anatomical features, e.g. bone structures, in the x-ray and MRI projection images and aligns the two.

In order to illustrate the preferred embodiment, an example is in order. A three dimensional MRI image is generated and used for preliminary planning, possibly days in advance of the treatment. A patient is imaged with real time MRI projection sequences as described, along candidate treatment trajectories. More specifically the operator chooses a gantry setting and a collimator setting. The conversion algorithm translates that information to the MRI machine and a beam's eye projection view is produced by the MRI machine for the operator to view. Furthering the example, the operator adjusts the table setting as he normally would. Normally, this action would physically move the patient table, but in the MRI simulator, the gradients are adjusted to produce images that mimic such movement of the patient. The operator adjusts different variables in this manner, until the treatment trajectory is selected. Optionally, a source (linac) to skin distance is also calculated as another quality control check to verify proper patient positioning during subsequent treatment.

In the preferred embodiment, the operator manipulates the variables to obtain a plurality of different paths to the malignancy. These paths are recorded and duplicated in subsequent treatment of the malignancy. In addition, the operator uses the unique capability of the magnetic resonance modality to discern the depth of the malignancy, hence to infer the distance between the linac source and the center of the malignancy. This distance is useful for subsequent dosimetric planning. Also, the MRI projection images are preferably projections through only a user specified thickness or slab perpendicular to the viewing direction containing the tumor.

In addition, extra image data is collected that shows the entire region exposed to the path of the beam. A slab parallel to the beam illustrates the skin to tumor depth and is useful for computing radiation dose to healthy tissue surrounding the malignancy without homogeneity correction. Selecting a field of view large enough to include the beam entrance and exit sites enables the beam trajectory to be set more precisely. Also, this data is used in post-processing to produce divergent portal image equivalents (sim films) to assist verification processes when positioning the patient in the linac. When the patient is positioned in the linac system and the beam aligned, a low dose image is collected, as if it were an x-ray imager. The x-ray projection image collected in this manner is aligned and compared to the MRI projection image produced on the simulator, to verify the proper alignment of the patient. Preferably, the MRI image data is collected using a sequence that shows bone clearly, to mimic an x-ray scan.

As an extra quality control check, after each trajectory has been established the oncologist measures the distance from the x-ray source to the skin of the patient (source-skin distance (SSD)) for each trajectory. A similar system of measurement is located in the linac, so that the SSD for each trajectory can be verified when the patient is being positioned in the linac.

One possible distance measurement technique is collecting an MR image parallel to the desired trajectory of the x-ray beam that has a field of view large enough to include the skin surface, and the tumor volume. Optionally, the exit point could also be visualized. The position of the entrance point is found in the MR simulator frame of reference, and by knowing its relation to the x-ray simulator, the SSD is found.

Another position locator system 70 in order to facilitate coordination of the patient's position in both the magnetic resonance apparatus and the linac, is contemplated. A plurality of lasers map points on the surface of the patient, which are duplicated by a similar array of lasers in the linac. Alternately, one remote laser is fiber-optically or otherwise split into a plurality of sources that serve the same purpose. Other position locating devices, such as sonic locators, have also been contemplated. It is to be appreciated that other position locating systems will be obvious to those skilled in the art.

Three distinct versions of the preferred embodiment are contemplated. The first version as envisioned, is the most similar to present day x-ray simulator systems. The controls are the same as an x-ray oncology simulator. Three dimensional infinite slabs are gathered that mimic beam's eye paths through the patient. This version is closest to an oncology simulator and therefore is most familiar to oncologists.

The second version involves all features of the first, adding options of slice selection and depth. Controls are similar, apart from added controls for slice and depth selection.

In the third version, once the malignancy is located, a volumetric, high-resolution image is obtained. This image is stored, then used later to plan treatment paths through the patient without the patient physically being present. Dosimetric information and sim films are also obtainable as described previously.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging system comprising:
   a magnetic resonance scanner for generating an image of at least a portion of a patient, the portion including a medical malignancy;
   a user interface including typical oncology linac controls for controlling a field of view of the magnetic resonance scanner;
   a coordinate conversion algorithm that converts input from the user interface from a linac coordinate system into a magnetic resonance scanner coordinate system to control performance a magnetic resonance imaging operation; and
   a video processor that withdraws selected portions of the image and converts them into appropriate form for human-readable display.

2. The diagnostic imaging system as set forth in claim 1, further including:
   a distance meter for measuring a distance from an x-ray source to an entry point on the patient.

3. The diagnostic imaging system as set forth in claim 1, wherein the user interface further includes slice width selection and depth selection controls.

4. The diagnostic imaging system as set forth in claim 3, wherein the user interface further includes a readout that displays a position of a field of view in coordinates of an oncology linac.

5. The diagnostic imaging system as set forth in claim 4, further including a plurality of laser beams with paths similar to paths of laser beams in the oncology linac.

6. A diagnostic imaging system comprising:
   a magnetic resonance scanner for generating an MRI image of at least a portion of a patient in an MRI scanner coordinate system, the patient portion including a medical malignancy;
   a user interface including typical oncology linac controls;
   a coordinate conversion algorithm circuit including:
      an input portion that accepts a linac control signal in the form of a gantry angle, a table position, and a collimator angle;
      a conversion processor which converts linac control inputs into the MRI scanner control outputs; and,
      an output portion that outputs MRI control signals;
   an MRI controller for controlling operations of the magnetic resonance scanner, the MRI controller being connected with the coordinate conversion algorithm output portion to receive output MRI control signals therefrom; and
   a video processor that withdraws selected portions of the MRI image and converts them into appropriate form for human-readable display.

7. A diagnostic imaging system comprising:
   a magnetic resonance scanner for generating an image of at least a portion of a patient, the portion including a medical malignancy;

a user interface including typical oncology linac controls;

a coordinate conversion algorithm that converts input from the user interface into a form usable by the magnetic resonance scanner;

a video processor that withdraws selected portions of the image and converts them into appropriate form for human-readable display;

a linear accelerator for generating an x-ray beam; and, an x-ray pick-up for converting intensities or radiation from the linear accelerator into an x-ray projection image, the x-ray pick-up being connected with the video processor for concurrent display of x-ray projection and magnetic resonance images.

8. The diagnostic imaging system as set forth in claim 7, wherein the magnetic resonance scanner generates MR projection images along at least one planned treatment trajectory and further including:

an alignment processor for aligning the MR projection image along the planned treatment trajectory.

9. A method of diagnostic imaging comprising:

using controls for an oncology linac to generate linac control signals that indicate a candidate treatment trajectory through a patient;

converting the linac control signals to control signals for a magnetic resonance apparatus;

generating an MR projection image along the projected treatment trajectory; and, displaying the MR projection image.

10. The method as set forth in claim 9, further including:

measuring a portion of the candidate trajectory from the linac to a point of entry on the patient.

11. The method as set forth in claim 9, wherein the step of generating the MR projection image includes one of:

generating a three dimensional magnetic resonance image and mathematically projecting the three dimensional magnetic resonance image along the candidate treatment trajectory; and, generating magnetic resonance data encoded along first and second linear coordinates with a third linear coordinate aligned with the candidate treatment trajectory.

12. The method as set forth in claim 9, further including:

identifying and locating a tumor within the patient;

generating MR projection images along a plurality of candidate trajectories through the tumor.

13. The method as set forth in claim 12, further including:

aiming a linac along one of candidate trajectories;

generating a low power x-ray projection image along the one candidate trajectory;

displaying the x-ray and MR projection images along the one candidate trajectory.

14. The method as set forth in claim 13, further including:

superimposing the x-ray and MR projection images along the one candidate trajectory.

15. The method as set forth in claim 14, further including:

adjusting at least a collimation of the linac in accordance with the superimposed image;

treating the tumor along the candidate trajectory with a high power x-ray beam from the linac.

16. The method as set forth in claim 13, further including:

adjusting at least a collimation of the linac in accordance with the superimposed image;

treating the tumor along the candidate trajectory with a high power x-ray beam from the linac.

17. The method as set forth in claim 16, wherein generating the MR projection image includes:

exciting resonance in a slab region with a thickness dimension of the slab region parallel to the candidate trajectory;

encoding the resonance along two dimensions of the slab region perpendicular to the thickness dimension and each other without encoding the resonance along the thickness dimension.

18. An oncological treatment system comprising:

a high power linear accelerator for irradiating a malignancy in a patient with a beam of radiation along each of a plurality of treatment trajectories with a selectable cross section;

a magnetic resonance apparatus for generating in a magnetic resonance coordinate system 3D magnetic resonance images that include the malignancy along each treatment trajectory;

a video processor which projects a selected magnetic resonance along a selected projection trajectory;

a conversion algorithm means for converting trajectory selecting signals from the linear accelerator into the magnetic resonance coordinate system, the conversion algorithm means being connected with the video processor to select the projection trajectory; and, a human readable display for displaying the projection images.

19. The oncological treatment system as set forth in claim 18, further including:

a distance meter for measuring a skin to source distance.

20. The oncological treatment system as set forth in claim 18, further including:

a position readout for displaying trajectory information.

21. An oncological treatment system comprising:

a high power linear accelerator for irradiating a malignancy in a patient with a beam of radiation along each of a plurality of treatment trajectories with a selectable cross section;

an x-ray pick-up for converting a wide cross section radiation beam from the linear accelerator into electronic data;

a reconstruction processor for generating a radiation projection image along the treatment direction from the electronic data;

a magnetic resonance apparatus for generating magnetic resonance projection images of the malignancy along each treatment trajectory.

22. The oncological treatment system as set forth in claim 21, further including:

an image alignment processor which superimposes the radiation projection image and one of the magnetic resonance projection images along a common treatment trajectory.

23. An MRI hardware upgrade comprising:

a control panel including linear accelerator gantry controls, patient table controls, and linear accelerator collimator controls similar to those of an oncology linear accelerator;

a conversion algorithm that mathematically converts control data from the gantry, table, and collimator controls in a linear accelerator gantry, table, and collimator coordinate system to MRI control signals for controlling scanning operations of a magnetic resonance apparatus to control at least one of field of view, slab thickness and orientation, slab depth, type of MRI sequence, and MRT image projection trajectory.

24. The MRI hardware upgrade as set forth in claim 23, further including:
a skin to source distance meter that measures a distance from a source of the linear accelerator to a point of entry on a patient.

25. The MRI hardware upgrade as set forth in claim 23, further including:
a display that describes a view in terms of a gantry variable, a table variable, and a collimator variable.

* * * * *